US008980619B2

(12) United States Patent
Upreti et al.

(10) Patent No.: US 8,980,619 B2
(45) Date of Patent: Mar. 17, 2015

(54) METHOD FOR BIO-ASSISTED TREATMENT OF HYDROCARBON CONTAMINATED SOIL

(75) Inventors: Manoj Kumar Upreti, Haryand (IN); Harinder Kaur Dua, Haryana (IN); Mahendra Pratap Singh, Haryana (IN); Arvind Pratap Singh, Haryana (IN); Ravinder Kumar Malhotra, Haryana (IN); Ram Prakash Verma, Haryana (IN)

(73) Assignee: Indian Oil Corporation Limited, Mumbai (IN)

( * ) Notice: Subject to any disclaimer, the term of this patent is extended or adjusted under 35 U.S.C. 154(b) by 1308 days.

(21) Appl. No.: 12/375,892

(22) PCT Filed: Sep. 18, 2006

(86) PCT No.: PCT/IN2006/000374
§ 371 (c)(1),
(2), (4) Date: May 6, 2009

(87) PCT Pub. No.: WO2008/015688
PCT Pub. Date: Feb. 7, 2008

(65) Prior Publication Data
US 2009/0325271 A1 Dec. 31, 2009

(30) Foreign Application Priority Data

Jul. 31, 2006 (IN) .......... 1207/MUM/2006

(51) Int. Cl.
*A62D 3/00* (2006.01)
*B09C 1/10* (2006.01)
*C12P 1/04* (2006.01)
*C12R 1/385* (2006.01)
*C12R 1/125* (2006.01)
*A62D 3/02* (2007.01)
*C02F 3/34* (2006.01)
*C12R 1/40* (2006.01)

(52) U.S. Cl.
CPC ... *B09C 1/10* (2013.01); *C12P 1/04* (2013.01); *C12R 1/385* (2013.01); *C12R 1/125* (2013.01); *A62D 3/02* (2013.01); *C02F 3/34* (2013.01); *C12R 1/40* (2013.01)
USPC ........ 435/262.5; 210/601; 210/606; 210/610; 210/611

(58) Field of Classification Search
CPC .............. B09C 1/10; C02F 3/34; A62D 3/02; C12P 1/04; C12R 1/01
USPC ................ 435/262.5; 210/601, 606, 610, 611
See application file for complete search history.

(56) References Cited

U.S. PATENT DOCUMENTS

| 4,401,569 | A | * | 8/1983 | Jhaveri et al. ................. 210/610 |
| 4,535,061 | A | * | 8/1985 | Chakrabarty et al. ..... 435/252.4 |
| 5,427,944 | A | * | 6/1995 | Lee et al. .................... 435/262.5 |
| 5,753,122 | A | * | 5/1998 | Taylor et al. .................. 210/611 |
| 5,958,241 | A | * | 9/1999 | DeBenedetto et al. ....... 210/611 |
| 6,057,147 | A | | 5/2000 | Overland et al. |
| 2002/0187545 | A1 | * | 12/2002 | Calcavecchio et al. ....... 435/262 |

* cited by examiner

*Primary Examiner* — Michael Hobbs
(74) *Attorney, Agent, or Firm* — Maschoff Brennan

(57) ABSTRACT

Provided is a method of treating a hydrocarbon-contaminated soil/gravel with a blend of microbes by adding a first microbe selected from the group consisting of *Pseudomonas aeruginosa* strain IOCX, *Pseudomonas aeruginosa* strain IOC DHT and mixtures thereof to a hydrocarbon-contaminated soil/gravel to release the hydrocarbon; and adding a second microbe selected from the group consisting of *Pseudomonas putida* strain IOC5al, *Pseudomonas putida* strain IOCR1, *Bacillus subtlis* and a mixture thereof to degrade the released hydrocarbon.

17 Claims, No Drawings

METHOD FOR BIO-ASSISTED TREATMENT OF HYDROCARBON CONTAMINATED SOIL

FIELD OF THE INVENTION

This invention in general relates to the method for treatment of hydrocarbon-contaminated soils. More particularly, the present invention provides a novel biological treatment for degradation of undesired contaminants in soil, flooded with water or in slurry form.

BACKGROUND OF THE INVENTION

The production, processing, storage, transportation, as well as unintentional spillage of crude oil and petroleum distillates has contributed to the release of hydrocarbon into the environment. This has resulted in large number of polluted sites and enormous volumetric quantities of soil, which have been contaminated with hazardous substances. Soil contamination can cause extensive damage to the local ecosystem by accumulating in the tissue of animals and plants and by causing death thereto and/or mutation to the progeny thereof. Such contamination can also present a serious health threat to humans, and, in extreme cases, can render the contaminated area unsuitable for human habitation.

The hydrocarbon-contaminated soil/storage pits are generally treated by secure landfill, incineration, indirect thermal treatment, aeration, venting, air sparging and conventional bioremediation. Sludge stored in storage pits and oil contaminated soil having large amount of stones/gravels/coarse material and free flowing water cannot be treated by these methods. In these areas the hydrocarbon oil present in sediment does not remain bio-available for microbial action and oil remain partitioned between water phase and solid soil/gravel particles.

There are many hydrocarbon-contaminated sites like near the riversides, low-lying areas, in the rain prone areas where hydrocarbon contaminated soil remain in the slurry form and water remains in free flowing conditions on the surface. These sites cannot be treated by conventional methods. The problem becomes much pronounced when such water-flooded hydrocarbon contaminated area contains large gravels and stones besides soil.

To have a successful treatment of oil-contaminated soil the release of hydrocarbon adsorbed on solid soil particles/gravel surface is essentially required. Various surfactants of chemical or biological origin are having ability to release oil from sediments. However, chemical surfactants owing to their toxicity towards microorganisms, particularly hydrocarbon degrading microbes and other adverse ecological impact are not used commonly and moreover, chemical surfactants are found less effective for sustained release of oil. Improved hydrocarbon release and degradation by addition of purified biosurfactant is reported in prior art (Rahman et al., Bioresource. Technology, 90, 159-168. 2003; Kuyukina et al., Environment International., 31,155-161, 2005). However, for field bioremediation application based on bioaugmentation, addition of the biosurfactant-producing bacteria may be beneficial and more practical than exogenously adding purified biosurfactant.

Dean and co-workers (*Journal of Environmental Quality* 30:1126-1133 (2001)) studied phenanthrene biodegradation by co-culture of phenanthrene degrading bacteria and bacteria having surfactant-producing strains in Fallsington sandy loam soil microcosms and aqueous medium, separately. The co-culture of contaminant-degrading and surfactant-producing bacteria resulted in the overall enhancement of phenanthrene degradation.

Van Hamme and Ward, (*Appl Environ Microbiol*. October; 67(10):4874-9, 2001.) studied the physical and metabolic interactions between *Rhodococcus* sp. strain F9-D79 and *Pseudomonas* sp. strain JA5-B45 were examined during growth on Bow River crude oil in 250-ml Erlemneyer flasks containing 50 ml of medium and reported a slight enhancement in TPH removal by the coculture than the individual bacterium. In the co-culture *Rhodococcus* sp. strain F9-D79 forms excellent, though transient, crude oil-water emulsions between 24 and 48 h of incubation. *Pseudonmonas* sp. strain JA5-B45 does not emulsify oil but does efficiently degrade crude oil.

U.S. Pat. No. 3,871,956 features a method for cleaning accidental oil spills on water or in soil. The method of this patent does not utilize temperature or oxygen controls and is not a self-perpetuating process.

U.S. Pat. No. 5,035,537, discloses a method for treatment of soil, porous rock and similar material contaminated by petroleum, hydrocarbon and volatile organic compounds and includes the steps of gathering the contaminated soil, disbursing it uniformly on an impervious horizontal surface to a depth of four to six inches, treating it with an emulsifying agent and allowing the emulsifying agent to seep through the soil and volatilize the hydrocarbon and organic compounds in the soil.

U.S. Pat. No. 5,055,196 discloses a process for treating soil or sludge to remove contaminants in contact with the soil or sludge. More particularly, this method relates to a process in which inorganic contaminants, such as metal or metal salts, or organic contaminants, such as PCBs, are removed from water-wet soil and sludge.

U.S. Pat. No. 5,059,252 discloses a method for on-site bioremediation of soils contaminated with petroleum derived hazardous wastes. This method for enhancing bioremediation includes the step of applying a cationic ion exchange resin to the contaminated soil in an amount sufficient to promote growth of organisms capable of degrading the hazardous waste.

U.S. Pat. No. 5,427,944 teaches a process for biodegrading polycyclic aromatic hydrocarbon contaminants using a mixed bacteria culture of *Achromobacter* sp. and *Mycobacterium* sp. and nutrient. The mixed bacteria culture was utilized for in situ or ex situ bioremediation of contaminated soil, or in any of various conventional bioreactors to treat contaminated liquids such as landfill leachates, groundwater or industrial effluents.

U.S. Pat. No. 5,453,133 relates to a process for removing contaminants, such as hydrocarbons, from soil. The process involves contacting the contaminated soil with a suitable solvent for the contaminant, in the presence of a bridging liquid, which is immiscible with the solvent, while agitating. The amount of the bridging liquid and the degree of agitation are balanced to control the particle size of the substantially contaminant-and solvent-free soil agglomerates so formed.

U.S. Pat. No. 5,494,580 relates to a method for decontamination of a hydrocarbon-polluted environment by the use of certain bacterial compositions.

U.S. Pat. No. 6,057,147 discloses an apparatus and method for enhanced bioremediation of hydrocarbons removed from a contaminated object. The device and method promote continuous microbial bioremediation of hydrocarbon contaminants in a self-propagating manner while cleaning the solution and filtering sediment without generating an environmentally dangerous waste trail. The cleaning solution comprises microorganisms of the genus *Achromobacter, Actinobacter*, Hlcaligene; *Arthrobacter, Bacillus, Nocardia, Flavobacterinm, Pseudoinonas* and mixtures thereof.

U.S. Pat. No. 6,652,752 discloses method for the biodegradation of an oil-based sludge comprising a mixture of petroleum hydrocarbons. The method comprises forming an aqueous solution in a reactor of an oil-in-water emulsion of the oil-based sludge, bacterial culture and nutrients for the bacterial culture, the bacterial culture having the ability to grow on petroleum hydrocarbons as sole carbon source and having been isolated from a hydrocarbon contaminated soil or hydrocarbon-containing sludge or other environments rich in hydrocarbon degrading bacteria, maintaining the aqueous solution under aerobic conditions in the reactor at a temperature of at least 10° C. for a period of time sufficient to reduce the amount of hydrocarbon by at least 25%, and discharging aqueous solution having a reduced amount of hydrocarbons from the reactor.

The United States Patent Application 20020187545 discloses a process for bioremediation of hydrocarbon-contaminated waste using corn material. The hydrocarbonaceous contaminant is contacted with the corn material in the presence of nutrients and bacteria effective for bioremediation.

The present invention teaches the art to decontaminate efficiently the oil-contaminated soil having soil with free flowing water over it or in soil-water slurry form and the hydrocarbon is either adsorbed in soil/gravel particles or present in the water-soil interface employing a blend of novel microbes.

SUMMARY OF THE INVENTION

It is a principal object of the present invention to provide a method for treatment of hydrocarbon-contaminated soil to enhance degradation of said contamination in an efficient and environmentally acceptable manner, wherein said method employs bio-assisted technique using selective microbes, through a combination of superior emulsification and degradation capabilities.

Further object of the present invention is to provide a method for treatment of hydrocarbon-contaminated soil to degrade said contamination, wherein said method is capable to perform effectively at low temperature as well as moderately high temperature.

Yet another object of the present invention is to provide a method for treatment of hydrocarbon-contaminated soil to degrade said contamination, wherein said method is capable in decontamination of gravel rich hydrocarbon contaminated soil having free flowing water or is in slurry form, by using a selective blend of biosurfactant producing and blend of hydrocarbon assimilating microbes.

Yet further object of the present invention is to provide a method for treatment of hydrocarbon-contaminated soil to degrade said contamination, wherein said method is enabling the remediation and removal of hydrocarbon, oily sludge, spilled oils, and slurries from said contaminated soil.

Yet another object of the present invention is to provide a method for treatment of hydrocarbon-contaminated soil to degrade said contamination, wherein a novel microbial consortia is selected, which is capable of producing efficient and effective tensio-active emulsifying agent biosurfactants and releasing oil from soil/gravel particles.

Yet further object of the present invention is selection of another novel microbe, which is capable of degrading oil in aqueous phase, aqueous-soil interface and in oil water interface.

The above and other objects are attained in accordance with the present invention wherein there is provided following embodiments, however the described embodiments hereinafter is in accordance with the best mode of practice and the invention is not restricted to the particular embodiments.

In accordance with one embodiment of the present invention, there is provided a method for treating hydrocarbon contaminated soil to remove the contamination, wherein said method comprises isolating the microbes capable of producing biosurfactant(s) employing suitable nutrient medium, adding said microbes into the contaminated sites to release adsorbed oil from soil/sediments/gravel, further adding another isolated microbes having capability of breaking down released hydrocarbon substances (e.g., crude oil, other petroleum distillates, either paraffin based or possessing other peculiar chemical bases) for remediation of hydrocarbon contaminated soils.

In accordance with another embodiment of the present invention, there is provided a method for treating hydrocarbon contaminated soil, wherein said biosurfactant producing microbes as well as the hydrocarbon degrading microbes are grown, separately in suitable vessels containing a suitable nutrient medium, further the appropriately grown mixed microbial culture of the invention is adsorbed on suitable carrier, wherein the carrier is able to retain microorganisms thereon relatively mildly and thus allows easy release of microorganisms thus proliferated.

In accordance with yet another embodiment of present invention, there is provided a bioassited method for treatment of hydrocarbon-contaminated soils, wherein the microbes used for releasing the oils are *Pseudomonas aeruginosa* strain IOCX or *Pseudomonas aeruginosa* strain IOC DHT and used alone or in combination thereof. Further the microbes used for degrading the released oil are *Pseudomonas putida* strain IOC5al or *Pseudomonas putida* strain IOCR1 or *Bacillus subtlis* and used alone or in combination thereof.

*Pseudomonas aeruginosa* strain IOCX, *Pseudomonas aeruginosa* strain IOC DHT, *Pseudomonas putida* IOC5al and *Pseudomonas putida* IOCR1 were deposited under the terms of the Budapest Treaty on the International Recognition of the Deposit of Microorganisms for the Purposes of Patent Procedure (submitted to IDA-MTCC on Dec. 17, 2007 as MTCC Nos. 5389, 5388, 5385 and 5387, respectively). All restrictions imposed by the depositor on the availability to the public of the deposited biological material will be irrevocably removed upon granting of a patent on the present application.

In accordance with another embodiment of the present invention, there is provided bioassisted methods for treatment of hydrocarbon-contaminated soils, wherein said microbes are capable of working in the temperature range of 3-45° C., preferably 10 to 35° C.

In accordance with yet another embodiment of the present invention, there is provided a bioassisted method for treatment of hydrocarbon-contaminated soils, wherein microbes for releasing the oils are inoculated before the microbes capable of degrading the released oils.

In accordance with still another embodiment of present invention, there is provided a bioassisted method for treatment of hydrocarbon-contaminated soils, wherein said microbes to release the oils is added not less than two weeks before the microbes to 20 degrade the released oils.

In accordance with yet another embodiment of present invention, there is provided a bioassisted method for treatment of hydrocarbon-contaminated soils, wherein the ratio of microbes used herein for releasing the oils and the microbes for degrading said released oils is in the range of 1:1 to 1:10, preferably in the range of 1:2.

DETAILED DESCRIPTION OF THE INVENTION

While this specification concludes with claims particularly pointing out and distinctly claiming that, which is regarded as the invention, it is anticipated that the invention can be more readily understood through reading the following detailed description of the invention and study of the included examples.

The present invention provides a safe, effective and inexpensive method for treating hydrocarbon-contaminated soil flooded with water or in the slurry form and wherein the contaminants are largely adsorbed with soil/gravel particles.

In the present invention there is provided the specific selection of a biosurfactant-producing microbes to release oil from the sediments and gravels and to make them bioavailable to the microbes having ability to degrade oil present in aqueous phase, aqueous-soil interface and in oil-water interface, for removal of oil. Further these microbes were active in a wide range of temperature and were able to grow temperature ranging from 3° C. to 45° C.

The biosurfactant producing microbes disclosed herein in the present invention were isolated by selective enrichment technique from hydrocarbon-contaminated soil. Isolation of the pure desired isolates was done by streaking on minimal salt agar medium containing hydrocarbon as carbon source. The biosurfactant producing ability was verified by doing various tests. Said microbes were selected based on their ability to produce efficiently biosurfactant in water soluble and insoluble carbon source at 3° C. as well as at 45° C. Further, the in situ biosurfactant production by the bacteria and its capability to release oil during growth on oil contaminated soil-water slurry was established. The extra cellular biosurfactant were also isolated from the microbes and its capability was established to release oil from soil sediments as well in oil-sand column. The bacteria as well as the purified biosurfactant could efficiently release oil from oil-water slurry.

The microbes were selected based on their ability to grow in crude oil/distillates/PAHs/alkanes in aqueous phase, aqueous-soil interface, in oil-water interface and soil sediments. In order to take the benefits of synergy of diverse metabolic potential of microbes, consortia of the three selected bacteria was constructed. The effect of the addition of biosurfactant producing bacteria and purified biosurfactant on the degradation of hydrocarbons was observed and significant increase in biodegradation was found. The consortia of biosurfactant producing and hydrocarbon degrading bacteria were evaluated in order to rule out any growth inhibition by one type of the bacteria on other type of bacteria and vice versa.

The minimum nutrient disclosed herein according to the present invention desirably includes a nitrogen source, such as an ammonium salt, and a phosphorus source, such as an alkali metal phosphate compound, a magnesium source, such as a magnesium salt, and can optionally include other nutrients such as sodium, calcium and iron salts. The preferred nutrient system comprises an ammonium salt and a phosphate compound, along with minor amounts of other conventional nutrients, wherein the molar ratio of elemental nitrogen to phosphorus is from about 5:1 to about 15:1, preferably from about 8:1 to about 12:1. Most preferred nutrient system for use during the process disclosed in the present invention includes ammonium chloride, from about 5 to about 20 parts by weight of hydrated magnesium sulfate ($MgSO_4.7H_2O$) per 100 parts by weight of ammonium chloride, from about 5 to about 20 parts by weight of sodium chloride per 100 parts by weight of ammonium chloride, and from about 15 to about 50, and more preferably from about 20 to about 30 parts by weight of monobasic potassium phosphate ($KH_2PO_4$) per 100 parts by weight of ammonium chloride and traces of vitamins and trace elements. Further said nutrients are dissolved in a suitable amount of water to dissolve the nutrients and combined with appropriate quantities of a suitable initial primary food source.

The biosurfactant producing microbes are two strains *Pseudomonas aeruginosa* strain IOCX and *Pseudomonas aeruginosa* strain IOC DHT. Further, the hydrocarbon degrading isolates showing highest growth and degradation potential are identified as *Pseudomonas putida* strain IOC5al, *Pseudomonas putida* strain IOCR1 and *Bacillus subtlis*.

*Pseudomonas aeruginosa* strain IOCX, *Pseudomonas aeruginosa* strain IOC DHT, *Pseudomonas putida* IOC5al and *Pseudomonas putida* IOCR1 were deposited under the terms of the Budapest Treaty on the International Recognition of the Deposit of Microorganisms for the Purposes of Patent Procedure (submitted to IDA-MTCC on Dec. 17, 2007 as MTCC Nos. 5389, 5388, 5385 and 5387, respectively). All restrictions imposed by the depositor on the availability to the public of the deposited biological material will be irrevocably removed upon granting of a patent on the present application.

The biosurfactant producing microbes as well as the hydrocarbon degrading microbes disclosed herein the present invention were grown, separately in a suitable vessel containing a nutrient solution. The vessel preferably contained control devices for temperature, pH, agitation, aeration and stirring. Particularly preferred nutrient system for growth includes (g per liter) yeast extract 5.0-10, $KH_2PO_4$, 0.5-1.0, $K_2HPO_4$ 0.5-1.0, $MgSO_4$ 0.5-1.0, $(NH_4)_2SO_4$ 0.25-0.75, $KNO_3$ 0.25-0.75, peptone 2.0-5.0, Fermentable sugars as carbon source 1-5%.

According to the present invention, microorganisms capable of degrading hydrocarbon contaminants and/or producing biosurfactant are dispersed in oil contaminated soil while being supported on, i.e., fixed in a carrier The carrier used herein is made of the materials that can retain microorganisms thereon relatively mildly and thus allow easy release of microorganisms thus proliferated. The carrier is inexpensive and can act as a nutrient source for the microorganisms thus applied, particularly a nutrient source, which can be gradually released to advantage. Further, the formation of a carrier by a biodegradable material is advantageous in that any problems arising from secondary contamination by residual carrier or the effect of applied microorganisms on the soil ecological system can be avoided. As such a biodegradable material is preferably used a carrier, which gradually decomposes and disappears after the remediation of soil by applied microorganisms. When carrier is used, applied microorganisms which have been released into soil after the disappearance of the carrier are then put in environments which are severe to growth such as competition with predominant native-born microorganisms in soil and predation by protozoan. The microorganisms are then driven out of soil and gradually decrease in number to extinction. As a result, the ecological system in soil can be restored to the original state. Preferred biodegradable carrier material used herein according to the present invention comprises cornhusk, sugar industry waste or any agricultural waste.

The carrier adsorbed microbial blend was tested for its efficacy in soil sample as such received from field at temperature of 3° C. and 45° C. First the biosurfactant producing blend (BS blend) was added and allowed to release the oil and subsequently the hydrocarbon degrading blend (HD blend) was introduced to degrade the oil. The ratio of BS blend and HD blend is from 1:1-1:10 (w/w), preferably 1:2.5.

A culture solution is used herein accordance with the present invention for the growth of microorganisms. Said culture solution comprises widely used material selected from meat juice, yeast extract, a malt extract, bactopeptone, glucose, inorganic salts or mineral or a mixture thereof. These components are mixed in a proper ratio depending on the kind of microorganism. As the nutrients any nutrient containing proper organic and inorganic nutrients besides the aforementioned culture solution, may be used. Preferable nutrient is mixture of yeast extract and potassium nitrate and ammonium phosphate in ratio of 2:1:0.1 to 1:0.1:0.01, most preferably 1:1:0.1.

In accordance with the present invention there is provided a use of aeration technique for remediation treatment of the contaminated soil, wherein frequent mechanical mixing and tilling of soil slurry can achieve proper aeration. The aeration can also be done by air sparging using some conventional devices known in the prior art. The rate of aeration may be ranging from 1 l/min to 25 l/min, preferentially 5 l/min, and preferentially 2 l/min. The temperature according to the present invention for soil remediation is from 3° C. to 45° C., preferably from 10° C. to 35° C., which is suitable for action of used microorganisms.

The following specific examples illustrate the process of this invention, but they should not be constructed as limiting the scope of the invention.

Example 1

Isolation of Biosurfactant Producing Bacteria Purification of Biosurfactant and Bacteria/Biosurfactant Mediated Oil Release The bacterial strains were isolated by the enrichment culture technique from the oil-contaminated soil. A 5 g sample of soil was inoculated into 100 ml of minimal salt medium (MSM) containing (per litre) 6.0 g of $Na_2HPO_4$, 3.0 g of $KH_2PO_4$, 1.0 g of $NH_4Cl$, 0.5 g of NaCl, 1.0 ml of 1 M $MgSO_4$, and 2.5 ml of a trace element solution ([per liter], 23 mg of $MnCl_2.2H_2O$, 30 mg of $MnCl_4.H_2O$, 31 mg of $H_3BO_3$, 36 mg of $CoCl_2.6H_2O$, 10 mg of $CuCl_2.2H_2O$, 20 mg of $NiCl_2.6H_2O$, 30 mg of $Na_2MoO_4.2H_2O$, and 50 mg $ZnCl_2$) (pH 7.0). Crude oil (5% w/v) was used as carbon source and incubated at 30° C. on a rotary shaker (200 rpm) for 4 days. After five cycles of such enrichment, 1 ml of the culture was diluted and plated on MSM agar (2% w/v) plates containing crude oil (5% w/v) as sole carbon source. The bacterial colonies obtained were farther purified on Luria-Bertani (LB) agar plates. The strain was stored as frozen stock cultures at −70° C. in 25% glycerol.

To study biosurfactant production and activity, bacteria were either grown in MSM containing water-soluble substrate like glucose (3%) and/or water insoluble substrate like 2% hexadecane. The cultures were incubated at 30° C. and 150 rpm, After 24 h the culture broth was centrifuged at 8000 rpm for 10 min and the supernatant was used for measurement of surface active properties. The surface-active compounds were extracted by liquid-liquid extraction from cell free culture broth acidified with 1 N HCl to pH 2.0. Supernatant fluid was mixed with an equal volume of chloroform:methanol (2:1) mixture. The solvent was evaporated and the material was used as crude biosurfactant and weighted to evaluate the yield.

BS producing microbes gave positive result in drop collapse and oil spreading test and significantly reduced the surface reduction on media (more than from 25 dN/cm). Interestingly, most of the surface-active activity of the strains was confined to the culture supernatant. Emulsification activities of the culture supernatant were measured with several water immiscible substrates and result showed that culture supernatant has high emulsification activities against diesel oil, kerosene, gas oil, crude oil and gasoline.

The biosurfactant-producing bacteria was adsorbed in the carrier matrix and inoculated ($3.0 \times 10^4$/ml) in the hydrocarbon contaminated soil-water slurry and oil release in the water phase was monitored by infrared spectroscopy following the solvent extract. The isolated biosurfactant (500 mg/l) was also evaluated in the same manner. The control was kept in the same experimental condition but without bacteria or biosurfactant. The results are as follows—

TABLE 1

Oil release during growth of BS blend and addition of isolated BS in soil-water slurry

| Condition | % Increased Oil release comparison to control, after 48 hrs | % Increased Oil release comparison to control, after 96 hrs |
|---|---|---|
| BS blend | 47 | 69 |
| Purified biosurfactant | 56 | 52 |

Example 2

Synergistic Oil Degradation by BS and HD Blend in Oil Contaminated Oil-Water Slurry at 10° C.

For contaminated oil-water slurry degradation tests, hydrocarbon contaminated soil-containing gravels and free flowing was obtained from field. One kilogram said soil-water slurry was inoculated with biosurfactant producing blend (BS blend), hydrocarbon degrading microbial blend (HD blend) and combination of both (applying BS blend first, then HD blend), separately. A 0.25% (w/w) yeast extract and 0.025% ammonium phosphate was added and kept at 10° C. An uninoculated control was also incubated under same conditions. The all sets were mixed for aeration and at timed interval oil release was monitored in water phase and a significant release in BS blend was observed. After a specified period whole sample was extracted with solvent (toluene) and hydrocarbon content was determined gravimetrically and by GC. The results are as follows:

| Treatment | % TPH reduction after six months |
|---|---|
| Control | 10 |
| BS blend | 19 |
| HD blend | 24 |
| BS blend followed by HD blend | 80 |

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope and spirit of this invention.

We claim:

1. A method of treating a hydrocarbon-contaminated soil/gravel with a blend of microbes, comprising:

adding a first microbe selected from the group consisting of *Pseudomonas aeruginosa* strain IOCX deposited with the MTCC as accession number 5389 *Pseudomonas aeruginosa* strain IOC DHT deposited with the MTCC as accession number 5388 and mixtures thereof to a hydrocarbon-contaminated soil/gravel to release the hydrocarbon; and adding a second microbe selected from the group consisting of *Pseudomonas putida* strain IOC5al deposited with the MTCC as accession number 5385, *Pseudomonas putida* strain IOCR1 deposited with the MTCC as accession number 5387, *Bacillus subtlis* and a mixture thereof to degrade the released hydrocarbon;

wherein the first microbe is added to the soil/gravel at least two weeks before the second microbe.

2. The method of claim 1, further comprising providing nutrients for the first microbe and the second microbe.

3. The method of claim 1, further comprising aerating the soil/gravel.

4. The method of claim 3, wherein the aerating is accomplished by periodic mixing of the soil/gravel.

5. The method of claim 3, wherein the soil/gravel is mixed with water to form a slurry and the slurry is periodically mixed.

6. The method of claim 3, wherein the aerating comprises air sparging the soil/gravel.

7. The method of claim 1, wherein the second microbe degrades the released hydrocarbon in an aqueous phase, aqueous-soil interface, oil-water interface or in a sediment.

8. The method of claim 1, wherein the hydrocarbon-contaminated soil contains water ranging from 1000 ppm to water present in flooded condition on the surface.

9. The method of claim 2, wherein the nutrients used in the method is selected from a nitrogen source, a phosphorus source, a magnesium source.

10. The method of claim 9, wherein the molar ratio of elemental nitrogen to phosphorus is from about 5:1 to about 15:1.

11. The method of claim 9, wherein the molar ratio of elemental nitrogen to phosphorus is from about 8:1 to about 12:1.

12. The method of claim 1, wherein the first microbe and the second microbe are supported on a carrier.

13. The method of claim 12, wherein the carrier is preferably selected from cornhusk, sugar industry waste or any agricultural waste.

14. The method of claim 1, wherein the first microbe and the second microbe are capable of working at the temperature range of 3° C. to 45° C.

15. The method of claim 14, wherein said microbes are capable of working preferably at the temperature range of 10° C. to 35° C.

16. The method of claim 1, wherein the ratio of the first microbe and the second microbe is 1:1 to 1:10.

17. The method according to claim 1, wherein the ratio of the first microbe and the second microbe is 1:2.

* * * * *

UNITED STATES PATENT AND TRADEMARK OFFICE
CERTIFICATE OF CORRECTION

PATENT NO. : 8,980,619 B2  
APPLICATION NO. : 12/375892  
DATED : March 17, 2015  
INVENTOR(S) : Upreti et al.

Page 1 of 1

It is certified that error appears in the above-identified patent and that said Letters Patent is hereby corrected as shown below:

On the Title Page, Item (75), under "Inventors", in Column 1, Line 1,
delete "Haryand" and insert -- Haryana --, therefor.

On the Title Page, Item (57), under "ABSTRACT", in Column 2, Line 9,
delete "subtlis" and insert -- subtilis --, therefor.

In the Claims

In Column 9, Line 12, in Claim 1, delete "subtlis" and insert -- subtilis --, therefor.

Signed and Sealed this
First Day of September, 2015

Michelle K. Lee
*Director of the United States Patent and Trademark Office*